United States Patent [19]
Shirley et al.

[11] Patent Number: 4,784,154
[45] Date of Patent: Nov. 15, 1988

[54] INTERFERENCE RESISTANT BIOMEDICAL TRANSDUCER

[75] Inventors: Donald J. Shirley, Boerne; Merle E. Converse, Helotes, both of Tex.

[73] Assignee: Colin Electronics Co., Ltd., Komaki, Japan

[21] Appl. No.: 929,988

[22] Filed: Nov. 13, 1986

[51] Int. Cl.[4] .............................................. A61B 5/02
[52] U.S. Cl. ..................................... 128/715; 381/67; 381/190; 310/310; 310/358; 128/773
[58] Field of Search .............. 128/640, 715, 773, 660; 310/324, 358; 381/67, 173, 190, 191, 169, 158

[56] References Cited

U.S. PATENT DOCUMENTS

| | | | |
|---|---|---|---|
| 1,131,741 | 3/1915 | Karmann et al. | 381/190 |
| 2,242,756 | 5/1941 | Pope | 381/190 |
| 3,153,123 | 1/1960 | Harman | 381/158 |
| 3,405,288 | 2/1966 | Dittrich | 128/715 |
| 3,710,465 | 1/1973 | Thomann | 310/358 |
| 3,858,575 | 1/1975 | Rose | 128/715 |
| 3,867,925 | 2/1975 | Ersek | 128/715 |
| 3,868,954 | 3/1975 | Ueda | 381/67 |
| 4,079,213 | 3/1978 | Bage et al. | 381/190 |
| 4,258,229 | 3/1981 | Eggert et al. | 128/773 |
| 4,295,009 | 10/1981 | Weidler | 310/324 |
| 4,374,377 | 2/1983 | Saito et al. | 310/324 |
| 4,475,014 | 10/1984 | King | 381/190 |
| 4,672,976 | 6/1987 | Kroll | 128/715 |

FOREIGN PATENT DOCUMENTS 520329  3/1955  Italy ................................ 128/773

Primary Examiner—William E. Kamm
Assistant Examiner—Timothy Keegan
Attorney, Agent, or Firm—Hamilton, Smith & Clarkson

[57] ABSTRACT

An interference resistant biomedical transducer for monitoring the acoustic output of a patient's cardiac or respiratory system which provides a high degree of rejection of acoustic noise and spurious electromagnetic signals. The transducer comprises a piezoelectric diaphragm assembly having electrodes which produce a differential output signal. The transducer housing includes a massive metal disc and a compliant handle which provide a mechanical filter to remove undesired signals such as those related to motion of the patient and ambient acoustic noise.

14 Claims, 3 Drawing Sheets

INTERFERENCE RESISTANT BIOMEDICAL TRANSDUCER

FIELD OF THE INVENTION

The present invention relates generally to the field of transducers. More specifically, the present invention provides an improved biomedical transducer for monitoring the acoustic output of a patient's heart or respiratory system while providing a high degree of rejection of ambient acoustic noise and spurious electromagnetic signals.

BACKGROUND

In the experimental study of cardiac functions and in many clinical situations, it is often necessary to monitor the acoustic output of a patient's heart at the exterior surface of the chest cavity. Such measurements are generally difficult to make because the acoustic signals produced by the heart are very weak. Detection of these cardiac acoustic signals is often complicated by acoustic signals caused by motion of the patient and interference caused by airborne noise. In addition, ambient electromagnetic interference picked up by the patient's skin and by interconnecting cables can create spurious signals which interfere with the performance of the transducer.

Another common application for an acoustic biomedical transducer is in connection with the monitoring of a patient's respiration system. For this monitoring application, an acoustic transducer is placed in either the suprasternal notch or the supraclavicular region to detect acoustic signals corresponding to the patient's respiration. The transducer used in this type is generally similar to that used for cardiac system monitoring and, further, is susceptible to the same types of difficulties as those discussed above.

Previous transducers for monitoring acoustic signals related to cardiac functions and respiration have been ineffective in overcoming the difficulties discussed above. A common problem with previous transducers is related to their relatively light weight. Such transducers lack sufficient motional stability to avoid erroneous detection of cyclic movements of the patient's chest as an acoustic signal related to the functioning of the heart or respiratory system. Another common problem with prior transducers is that minute movements of the technician's hand can be erroneously detected as an acoustic cardiac or respiratory signal. Further, such transducers are often susceptible to detection of ambient acoustic signals which are transmitted through the rear of the transducer assembly.

An effective transducer for the applications described above must have a very high sensitivity to tissue-conducted acoustic signals across a broad spectrum, but must have a very low sensitivity to other acoustic signals, such as those caused by patient motion and airborne sound. Furthermore, the transducer must have a very low sensitivity to electromagnetic interference. In addition to the technical requirements discussed above, it is very important that the transducer be easily cleaned and sterilized. The prior art is lacking a biomedical transducer which meets the requirements discussed above.

SUMMARY OF THE INVENTION

The biomedical transducer of the present invention overcomes the difficulties of previous transducers by providing an acoustic transducer which has a very high sensitivity to tissue conducted acoustic signals, low sensitivity to patient motion and a very low sensitivity to ambient airborne noise and spurious electromagnetic signals.

The biomedical transducer provided by the present invention comprises a thin acoustically sensitive diaphragm assembly mounted in a rugged, easily handled metal housing. The diaphragm assembly includes a circular flat plate piezoelectric bender transducer having an electrical polarization and electrode placement such that its output signal is differential with respect to ground. The arrangement of the diaphragm within the housing is such that the output signal is completely shielded from external electromagnetic fields. The transducer housing is relatively massive and, therefore, provides motional stability to prevent unintentional detection of body movements as acoustic signals. Furthermore, a compliant handle attached to the housing provides a means for a medical technician to maintain the transducer in the desired position without inadvertently transmitting vibrations to the transducer diaphragm assembly. The transducer housing of the preferred embodiment is formed of stainless steel or another suitable metal which can be easily cleaned and sterilized.

DETAILED DESCRIPTION OF THE PREFERRED EMBODIMENT

Figure 2:
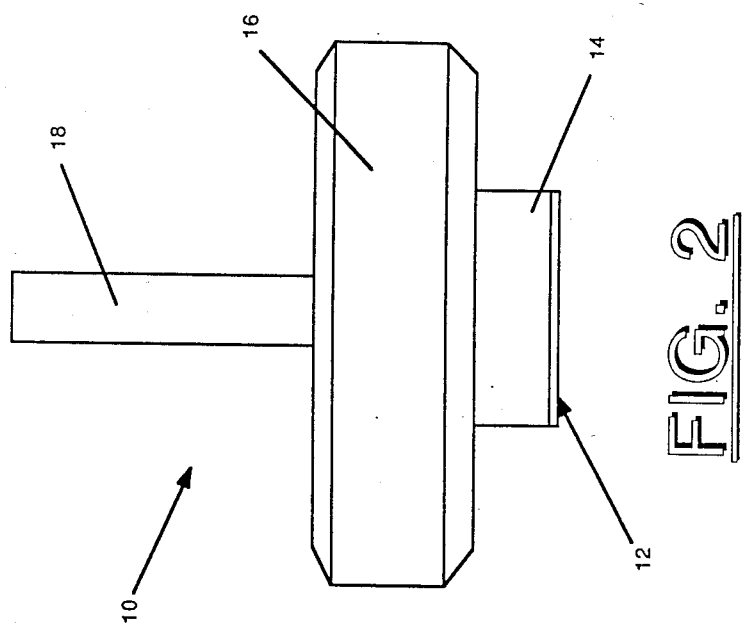
FIG. 2 is an elevational side view of the housing for the biomedical transducer of the present invention.
Figure 1:
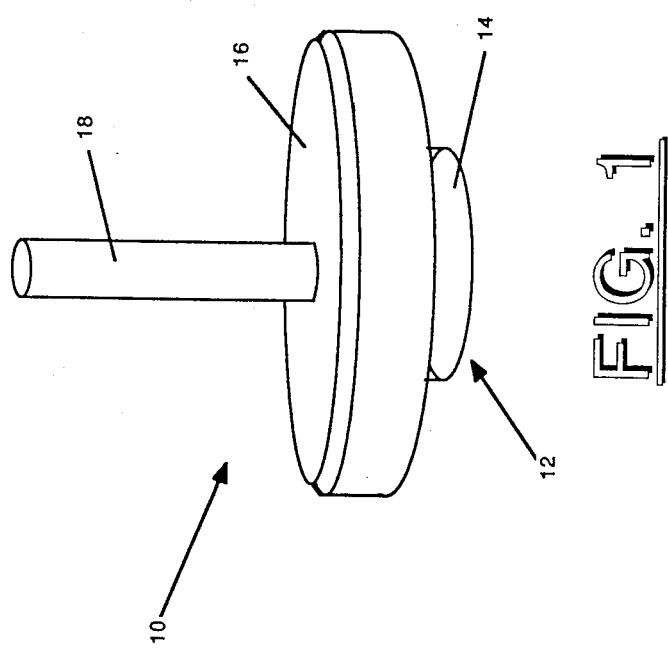
FIG. 1 is a perspective view of the housing assembly for the biomedical transducer of the present invention.

Referring to the drawings in more detail and to FIGS. 1 through 4 in particular, the interference resistant biomedical transducer 10 of the present invention is shown in its preferred embodiment. The transducer 10 comprises a diaphragm assembly 12, described in greater detail hereinbelow, which is contained within a transducer housing 14 having a cavity adapted to contain electrical connections for the diaphragm assembly. The transducer housing 14 comprises a generally cylindrical metal container, the upper portion of which is attached to one side of a massive metal disc 16. The diaphragm assembly 12 is mounted in the lower portion of the housing 14, as shown in FIG. 1, with the associated electrical components contained within the internal cavity of the housing. A compliant handle 18 is attached to the upper surface of the disc 16, as shown in FIGS. 1 and 2, to allow a medical technician to operate the transducer without inadvertently transmitting vibrations which might be erroneously detected as acoustic signals. The transducer housing 14 and the metal disc 16 are formed of stainless steel or another suitable metal which can be properly sterilized for use in clinical applications. The compliant handle 18 can be formed from a flexible metal shaft or spring which is covered with a rubber material.

In the preferred embodiment, the disc 16 has a mass of approximately one kilogram. The metal disc 16 thus provides sufficient mass to serve as a mechanical low pass filter. Additional mechanical filtering is provided by the compliant handle 18 which dampens any undesired acoustic signals caused by the medical technician when holding the transducer in contact with the patient. The mass of the disc 16 used in the preferred embodiment has been found to provide excellent motional stability without causing undue discomfort to a patient. The resonant frequency of the transducer assembly, when placed on the chest of a patient, is well below the low-frequency end of the response curve of the transducer. Thus, in the transducer output range, the disc 16 provides mechanical position stability which reduces the movement of the transducer 10. This stability leads to an increase in the signal output of the transducer in the desired range of frequencies. A second major function of the metal disc 16 is to reduce the transducer response to acoustic signals arriving from the rear of the housing. Such acoustic signals are suppressed by the large mass of the disc, thus reducing the movement of the transducer housing with respect to the diaphragm. A third function of the disc 16 is to reduce the coupling of vibrations from the technician's hand to the transducer assembly. Again, the mass of the disc 16 and the compliant handle 18 operate in conjunction to provide a mechanical low-pass filter to remove such signals.

Figure 4:
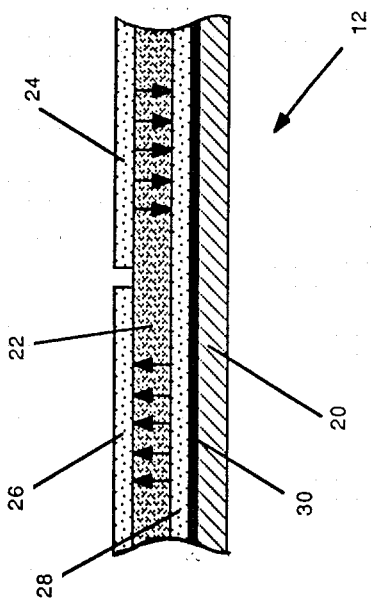
FIG. 4 is an elevational cross-sectional side view of the transducer diaphragm assembly showing details relating to the placement of the electrodes on the piezoelectric ceramic disc.
Figure 3:
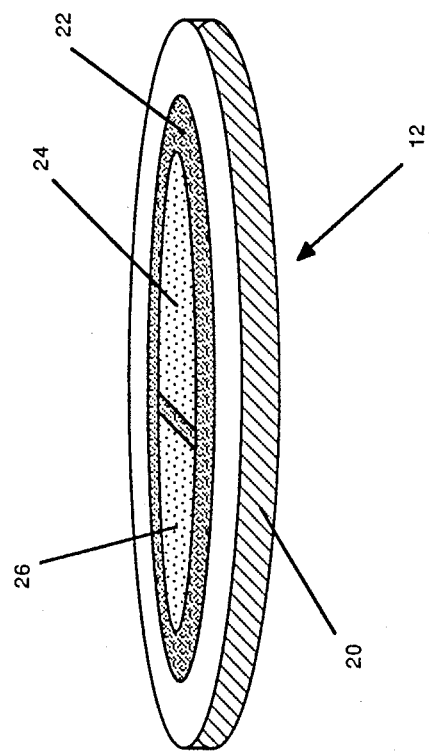
FIG. 3 is a perspective view of the transducer diaphragm assembly of the present invention.

Details relating to the transducer diaphragm assembly 12 can be seen by referring to FIGS. 3 and 4. The diaphragm assembly of the preferred embodiment comprises a generally circular metal disc or plate 20 having a thin circular ceramic piezoelectric disc 22 attached to one side thereof. Physical movement of the plate 20 in response to acoustic signals is translated by the piezoelectric disc into an electric output signal which can be correlated with the acoustic signal, as described below. Transducers employing piezoelectric plates as described above are normally termed flat plate bender transducers, commonly sold under the tradename Biomorph ®. The general design of such transducers is well known. However, the present invention provides a novel concept for connecting electrodes to a piezoelectric diaphragm in a configuration which causes it to serve as a transducer having a differential signal output. Such a transducer can be totally shielded from external electromagnetic fields, as will be described in greater detail below.

The piezoelectric ceramic disc 22 has electrodes attached to both its front and rear faces. Two semi-circular electrodes, 24 and 26, are attached to the front face of the disc 22, as can be seen in FIG. 3. A circular electrode 28 is attached to the rear face of disc 22, as shown in FIG. 4. The electrodes 24 and 26 have opposite polarities, for example electrode 24 being positive and electrode 26 being negative. The piezoelectric ceramic disc 22 is polarized such that the portions underlying each of the electrodes 24 and 26 will be polarized in opposite directions. The direction of polarization characteristics of the preferred embodiment of the ceramic disc 22 are illustrated by the arrows shown in FIG. 4.

Typically, the various plates of the diaphragm assembly are attached using an epoxy adhesive. The inner electrode 28 is electrically connected to the metal disc 20 through the use of a layer of conductive epoxy 30 or by small metal particles in the epoxy cement. Dimensionally, the diaphragm assembly comprises a metal disc 20 which is approximately 0.01 inch thick and approximately 1.25 inches in diameter. The ceramic plate 22 is typically 0.01 inch thick and 1.0 inch in diameter. In the preferred embodiment, the electrodes 24, 26 and 28 are formed from a fired-on silver-glass frit which is approximately 0.001 inch thick. The dimensions of the assembly components described above affect the resonance frequency of the device and thus its spectral bandwidth. The specific dimensions can, therefore, be chosen to provide a particular resonance frequency tailored to a specific application. A biomedical transducer diaphragm assembly having the above dimensions has a free air resonance of approximately 7 kilohertz.

Figure 5B:
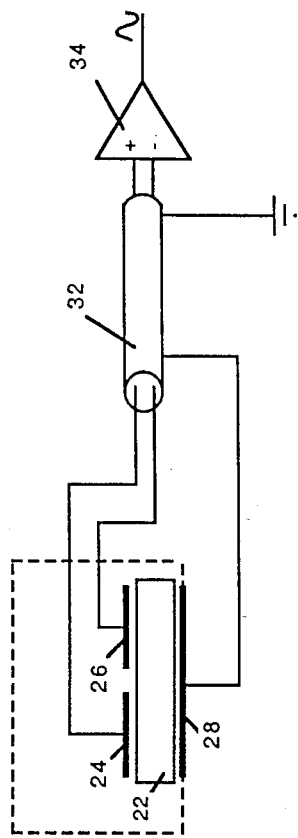
FIG. 5b is a schematic representation of the piezoelectric transducer assembly provided by the present invention.
Figure 5A:
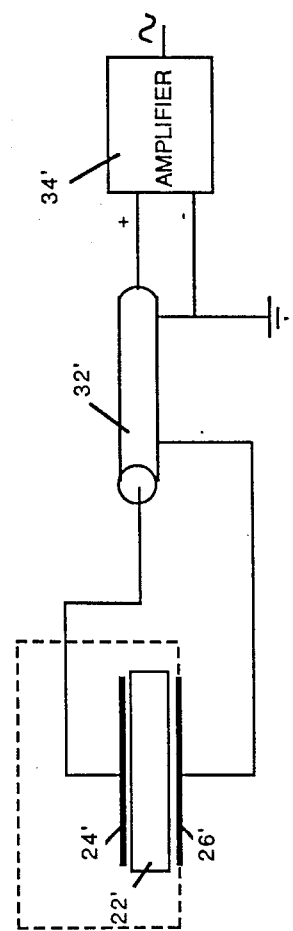
FIG. 5a is a schematic representation of a conventional piezoelectric transducer assembly.

The electrical connections of the diaphragm assembly are shown schematically in FIGS. 5a and 5b. The circuit illustrated in FIG. 5a is typical of prior transducers, while the circuit illustrated in FIG. 5b is descriptive of the transducer of the present invention. The dotted lines in each of the figures represent the electrical shielding provided by an appropriate housing, such as the transducer housing 14 of the preferred embodiment, shown in FIGS. 1 and 2. The circuit shown in FIG. 5a comprises a flat plate bender transducer having electrodes 24' and 26' on opposite sides of a piezoelectric plate 22'. The positive electrode 24' is connected to the inner conductor of a coaxial cable 32' which is further connected to an appropriate amplifier 34'. The transducer assembly of the preferred embodiment comprises first and second electrodes 24 and 26, respectively, attached to one face of the piezoelectric plate 22, shown in FIG. 5b, with a third electrode attached to the opposite face. As was discussed above, the portion of the piezoelectric ceramic disc 22 underlying the first electrode 24 and the portion underlying the second electrode 26 are polarized in opposite directions. This polarization causes the electrodes to have a differential signal output which can be used to reject electromagnetic interference, as discussed below.

The circuit shown in FIG. 5a will function with the same sensitivity as the circuit in FIG. 5b, however, the circuit shown in FIG. 5a does not have any provision for cancellation of the electrical noise picked up by the transducer element. The limited shielding provided by the enclosure and the coaxial cable will allow a low amplitude of radiated noise to be picked up by the signal electrode and the associated signal lead. By contrast, the transducer of the present invention provides two signals having a 180-degree phase difference. Both of these signals are shielded by the transducer housing and the shielded two-conductor cable. The signals on the two active lines have a 180-degree phase difference, while any radiated noise that is picked up has zero phase difference. Thus when the signals are connected to the differential input amplifier 34, the desired signal is amplified but the undesired noise is cancelled.

Operation of the transducer assembly can be seen by referring again to FIGS. 3 and 4. When the transducer assembly is in intimate contact with the tissue of the patient's chest, acoustic waves travelling from the heart impinge on the metal plate 20, thus causing minute forces to be applied perpendicular to the plane of the diaphragm assembly 12. Since the circumferential edge of the diaphragm assembly 12 is clamped within the transducer housing 14, the forces from the acoustic waves cause the center of the diaphragm assembly to move in and out with respect to the circumferential edge of the assembly. The movement of the diaphragm assembly thus generates a bending of the metal-ceramic layers, which causes the piezoelectric disc 22 to be alternately stretched and compressed in a radial direction. Because the ceramic disc 22 is piezoelectric, the radial stresses create electric signals which are collected by the electrodes and applied to an electronic amplifier through appropriate interconnecting cables. As was discussed above, portions of the piezoelectric ceramic disc 22 underlying the electrodes 24 and 26 are polarized in opposite directions. The signals produced by these electrodes will be equal in amplitude, but 180 degrees different in phase, thus producing a differential output which can be used to reject undesired electromagnetic interference, as described above. The present invention thus provides an effective biomedical transducer having a very high sensitivity to tissue conducted acoustic signals, while having a very low sensitivity to undesired acoustic signals and electromagnetic interference.

While the interference-resistant biomedical transducer of the present invention has been described in connection with the preferred embodiment, it is not intended to be limited to the specific form set forth herein, but on the contrary, it is intended to cover such alternatives, modifications, and equivalents as may be included within the spirit and scope of the invention as defined by the appended claims.

We claim:

1. An interference-resistant transducer for monitoring acoustic signals, comprising:
   a piezoelectric diaphragm having first and second sides, said diaphragm having one portion polarized in a first direction and another portion polarized in a second direction;
   means for communicating an acoustic signal to said piezoelectric diaphragm to cause movement thereof, said piezoelectric diaphragm producing an electrical signal in response to said movement;
   first and second electrodes on said first side of said piezoelectric diaphragm, said first and second electrodes having opposite polarities, said first electrode being aligned with said portion of said piezoelectric diaphragm polarized in said first direction, said second electrode being aligned with said portion of said piezoelectric diaphragm polarized in said second direction;
   a third electrode on said second side of said piezoelectric diaphragm, said third electrode being aligned with said first and second electrodes in a configuration to cause said first and second electrodes to produce a differential output signal in response to the movement of said diaphragm; and
   means for amplifying said differential output signal to provide an electrical representation of said acoustic signal.

2. A transducer according to claim 1, said means for communicating said acoustic signal comprising a flexible metal plate, said plate being adapted to flex in response to acoustic signals travelling in a direction normal to the plane of said disc.

3. A transducer according to claim 2, said piezoelectric diaphragm comprising a ceramic disc.

4. A transducer according to claim 3, said first and second electrodes comprising first and second layers of conductive material deposited on said first side of said ceramic disc.

5. A transducer according to claim 4, said third electrode comprising a circular layer of conductive material deposited on said second side of said ceramic disc, said third electrode being interposed between said piezoelectric diaphragm and said flexible metal plate.

6. A transducer according to claim 5, further comprising a layer of conductive epoxy between said third electrode and said flexible metal plate.

7. A transducer according to claim 6, said first and second electrodes and said third electrode comprising a fired-on layer of silvered-glass frit.

8. A transducer according to claim 7, said transducer having a resonant frequency of 7 kilohertz.

9. A transducer assembly for monitoring acoustic signals, comprising:
   a housing adapted to receive an acoustic diaphragm assembly;
   an acoustic diaphragm assembly received in said housing, said diaphragm assembly adapted to produce an electrical output signal in response to detection of an acoustic signal produced by a body;
   mechanical filtering means for filtering ambient acoustic signals and preventing detection of said ambient acoustic signals by said acoustic diaphragm assembly; said mechanical filtering means is a metal disc for maintaining positional stability of said transducer assembly with respect to the body from which said acoustic signal is detected, said metal disc being formed from stainless steel and having a mass of approximately one kilogram;
   a compliant handle attached to said housing, being formed from a flexible metal shaft, said handle cooperating with said metal disc to prevent ambient acoustic signals from being detected by said diaphragm assembly.

10. A transducer according to claim 9, said acoustic diaphragm assembly comprising a piezoelectric diaphragm movable in response to acoustic signals, said piezoelectric diaphragm being polarized in a manner to produce an electrical differential output signal.

11. An interference-resistant transducer for monitoring acoustic signals, comprising:
   a housing adapted to receive a diaphragm assembly;
   a diaphragm assembly received in said housing, said diaphragm assembly comprising a piezoelectric diaphragm having first and second sides, said diaphragm having one portion polarized in a first direction and another portion polarized in a second direction;
   means for communicating an acoustic signal to said piezoelectric diaphragm to cause movement thereof, said piezoelectric diaphragm producing an electrical signal in response to said movement;
   mechanical filtering means for filtering ambient acoustic signals to prevent said ambient acoustic signals from causing movement of said piezoelectric diaphragm;
   first and second electrodes on said first side of said piezoelectric diaphragm, said first and second electrodes having opposite polarities, said first electrode being aligned with said portion of said piezoelectric diaphragm polarized in said first direction, said second electrode being aligned with said portion of said piezoelectric diaphragm polarized in said second direction;

a third electrode on said second side of said piezoelectric diaphragm, said third electrode being aligned with said first and second electrodes in a configuration to cause said first and second electrodes to produce a differential output signal in response to the movement of said diaphragm; and means for amplifying said differential output signal to provide an electrical representation of said acoustic signal.

12. A transducer according to claim 11, each of said first and second electrodes and said third electrode comprising a fired-on layer of silvered-glass frit deposited on said first and second sides, respectively, of said piezoelectric diaphragm.

13. A transducer according to claim 11, said mechanical filter comprising a metal disc connected to said housing, said disc being formed from stainless steel and having a mass of approximately one kilogram.

14. A transducer according to claim 13, said housing further comprising a compliant handle attached thereto, said handle being formed from a flexible metal shaft, said handle cooperating with said metal disc to prevent ambient acoustic signals from being detected by said diaphragm assembly.

* * * * *